United States Patent [19]

Stollar et al.

[11] Patent Number: 4,871,882

[45] Date of Patent: Oct. 3, 1989

[54] PROCESS FOR THE PREPARATION OF DECABROMODIPHENYL ETHER WITH IMPROVED THERMAL STABILITY

[75] Inventors: Hyman Stollar; Khaim Khariton; Mark Grinberg; Eva Ellmann, all of Beer-Sheva, Israel

[73] Assignee: Bromine Compounds Limited, Israel

[21] Appl. No.: 107,959

[22] Filed: Oct. 13, 1987

[30] Foreign Application Priority Data

Oct. 22, 1986 [IL] Israel ............................. 80391

[51] Int. Cl.[4] ............................................. C07C 41/20
[52] U.S. Cl. ........................................ 568/639; 568/635
[58] Field of Search ................................. 568/635, 639

[56] References Cited

U.S. PATENT DOCUMENTS 4,521,633  6/1985  Pedjac ................................. 568/639

FOREIGN PATENT DOCUMENTS

| 2236362 | 2/1974 | Fed. Rep. of Germany | 568/639 |
| 0039639 | 3/1977 | Japan | 568/639 |
| 0222043 | 12/1983 | Japan | 568/639 |
| 147383 | 5/1977 | United Kingdom | 568/639 |
| 2143521 | 2/1985 | United Kingdom | 568/639 |

*Primary Examiner*—Werren B. Lone
*Attorney, Agent, or Firm*—Lerner, David, Littenberg, Krumholz & Mentlik

[57] ABSTRACT

A process for the preparation of Decabromodiphenyl ether is disclosed, which employs dibromomethane as the reaction medium, at temperatures not exceeding 80° C.

The product obtained by the process of the invention possesses improved thermal stability.

6 Claims, No Drawings

PROCESS FOR THE PREPARATION OF DECABROMODIPHENYL ETHER WITH IMPROVED THERMAL STABILITY

BACKGROUND OF THE INVENTION (a) The Field of The Invention

The present invention relates to a process for the preparation of Decabromodiphenyl ether having improved thermal stability.

Decabromodiphenyl ether, hereinafter referred to as "DECA" for the sake of brevity, is a well known flame retardant agent, useful in the preparation of articles made of polymeric material, to which it is desired to impart flame-retardant properties.

(b) The Prior Art

The art is crowded with processes for preparing DECA in a variety of solvents, ranging from liquid bromine to halogenated organic solvents. U.S. Pat. No. 4,521,633 discloses one of such processes in which DECA is prepared by reacting diphenyl ether in methylene chloride with a brominating agent in the presence of a catalyst, by initiating the reaction at a temperature of 15° C. or lower, and then raising the temperature of the reaction mixture to an elevated temperature, typically the solvent reflux temperature.

U.S. Pat. No. 3,959,387 discloses a process for the preparation of polybrominated biphenyl oxides in which the reaction is carried out in methylene bromide as the solvent, at temperatures of from room temperature to 200° C.

SUMMARY OF THE INVENTION

It has now been surprisingly found, and this is an object of the present invention, that it is particularly advantageous to employ dibromomethane as the reaction solvent, when operating according to the process of the invention.

It has further been found, and this is another object of the invention, that there is a critical maximal temperature at which the reaction can be carried out in order to obtain a product having good thermal stability.

The thermal stability of a flame retardant agent such as DECA is a very important requirement. In order to be usefully employed as additives to various plastics, flame retardant agents must be colorless, since coloration of the flame retardant additive results in the change in color of the article which incorporates it. Thermal instability of the FR agent may result in its change from colorless to colored, when heated, for instance, during the incorporation process. In the case of DECA, this thermal instability derives from the presence of impurities which, when heated, change their color to pink-brown, thereby imparting color to the DECA. The nature of these impurities is not known, although it has been suggested that they may be due to a polymeric derivative of the dibromomethane or to a Friedel-Crafts alkylation product of DECA. However, once the impurities are present in the DECA they cannot be reduced to a harmless concentration by conventional methods such as washing and extraction. Furthermore, it is not economically feasible to recrystallize the DECA to remove impurities, because of its low solubility. It is therefore clear that thermal stability - resulting from a sufficiently low content or the absence of such impurities - is of paramount importance for obtaining articles containing DECA which have a color stability for normal uses.

DETAILED DESCRIPTION OF THE INVENTION

The process for the preparation of Decabromodiphenyl ether with improved thermal stability, according to the invention, is characterized in that diphenyl ether, or one or more partially brominated derivative(s) thereof, is reacted with a brominating agent in dibromomethane as the solvent, in the presence of a bromination catalyst the maximal reaction temperature being kept lower than 80° C.

A preferred embodiment of the invention, is characterized by the steps of:

(a) preparing a solution of a brominating agent and a bromination catalyst in dibromomethane;

(b) providing liquid diphenyl ether or a partially brominated derivative of diphenyl ether, or a mixture of two or more of such partially brominated derivatives, in molten form, or soluted in dibromomethane;

(c) adding the liquid diphenyl ether or diphenyl ether brominated derivative(s) to solution (a), thereby initiating the reaction;

(d) raising the reaction temperature, after completion of step (c) to a temperature equal to or lower than 80° C.; and (e) after completion of the reaction, recovering the Decabromodiphenyl ether.

It is of course possible to employ a solid starting material, instead of its molten or soluted form. This, however, while possible, is unpractical, as it will be apparent to a person skilled in the art. It should be noted that partially brominated derivatives of diphenyl ether usually comprise a mixture of differently brominated diphenyl ethers. Thus Octabromodiphenyl ether, for example, is actually a mixture containing an average content of eight bromine atoms per each diphenyl ether molecule.

According to a preferred embodiment of the invention, step (c) is carried out at a temperature lower than 25° C., preferably between −5° C. and 5° C. According to another preferred embodiment of the invention, step (d) is carried out at a temperature higher than about 55° C.

According to another preferred embodiment of the invention the brominating agent is bromine.

According to still another preferred embodiment of the invention the bromination catalyst is an aluminum catalyst selected from metallic aluminum, $AlCl_3$ and $AlBr_3$.

The amount of catalyst employed is, of course, dependent on the various results that it is desired to obtain, as it will be apparent to a person skilled in the art. It is however clear that a catalytically effective amount of catalyst must be employed. A typical diphenyl ether: catalist w/w ratio is about 17, but much higher or much lower ratios can be employed, as the skilled chemist will appreciate, depending on various parameters such as the amount of water present in the reaction mixture.

The process of the invention presents several important practical advantages. Firstly, dibromomethane is less volatile than other normally employed halogenated solvents, such as dichloromethane. Therefore less solvent is lost via entrainment in the by-product HBr gas stream. Secondly, no transhalogenation takes place, as it happens with chlorinated solvents and therefore no bromine value is lost as brominated solvents. Thirdly, HBr is a valuable by-product which is recovered and used. However, when chlorinated solvents are employed the HBr is contaminated by sensible amounts of HCl which must be removed by costly purification steps, before the by-product HBr can be used.

The addition of the diphenyl ether to a solution containing the catalyst, rather than the addition of the catalyst to the reactant, is important for several reasons. Addition of the catalyst as a solution requires an additional vessel for preparing the solution, some catalysts—e.g., AlCl$_3$ are not soluble in dibromomethane and further the addition of the catalyst may be dangerous, since a runaway reaction may result if the addition is carried out too quickly.

The above and other characteristics and advantages of the process of the invention will be better understood through the description of the following illustrative and non-limitative examples.

EXAMPLE 1

To a one-liter flask equipped with a mechanical stirrer, a dropping funnel, a thermometer and a reflux condensor there were added 430 ml of dibromomethane, 7.5 g of anhydrous AlCl$_3$ and 880 g of bromine (5.5 moles). The contents of the flask were cooled to 0° C. and a solution of 85 g (0.5 mole) of diphenyl ether in 20 ml of dibromomethane was added dropwise to the stirred mixture during 2 hours, while maintaining the temperature between 0° and 5° C. After addition of the solution was completed, the contents of the flask were heated to 75° C. and this temperature was maintained for 5 hours. Completion of the reaction was checked by HPLC analysis. At the end of this period 60 ml of water were added and the unreacted bromine was bleached by the addition of concentrated sodium bisulphite solution. The aqueous layer was separated and the organic phase was washed twice with 150 ml portion of water and was then neutralized with an aqueous sodium hydroxide solution. The mixture was filtered and a white product was obtained which was washed with water and dried in a vacuum oven at 70° C. for 2 hours. The product was analysed by HPLC and was found to contain 95% DECA (m.p. 302°–305° C.). Thermal stability was checked by heating the product in an oven for 2 hours at 280° C. Color deviation was checked by visual inspection as compared to an unheated specimen. After heating was completed no appreciable change of color was observed.

EXAMPLE 2 (COMPARATIVE)

Example 1 was repeated, with the exception that when the addition of the diphenyl ether solution was completed the contents of the flask were heated at temperatures between 80° C. and reflux (about 92° C.) for 2–5 hours, until completion of the reaction. The product was analysed by HPLC and was found to contain 95.5% DECA (m.p. 301°–303° C.). The resulting product was heated as before at 280° C. for 2 hours, after which period it became pink to brown colored.

EXAMPLE 3

Example 1 was repeated, but starting from octabromodiphenyl ether as the starting material. 100 gr of octabromodiphenyl ether and 76 gr of bromine (0.48 moles) were employed, together with 2 gr of anhydrous AlCl$_3$ catalyst and 85 ml of dibromoethane as the solvent. Addition of the reactant was carried out at 3° C. during 30 minutes. 120 gr of product containing 95.5% DECA were obtained, with a melting point of 301°–304° C.

The above examples have been given for the purpose of illustration and are not intended to be limitative. Many variations can be effected in the process of the invention. Addition temperatures can be changed, addition times of the reagents can be varied and different bromination catalysts can be employed, all without exceeding the scope of the invention.

What we claim is:

1. A process for the preparation of decabromodiphenyl ether comprising brominating one or more aromatic compounds selected from the group consisting of diphenyl ether and the partially brominated derivatives thereof in a reaction mixture including bromine, a bromination catalyst selected from the group consisting of aluminum, AlCl$_3$ and AlBr$_3$ and dibromomethane, whereby said decabromodiphenyl ether is produced having improved thermal stability.

2. The process of claim 1, including maintaining said reaction mixture at a temperature lower than about 80° C.

3. The process of claim 1, including providing said reaction mixture and adding said aromatic compound to said reaction mixture.

4. The process of claim 3, including providing said reaction mixture at a first temperature lower than about 25° C., and heating said reaction mixture to a second temperature lower than about 80° C. following the addition of said aromatic compounds.

5. The process of claim 4, wherein said first temperature is between about −5° C. and 5° C.

6. The process of claim 2, wherein said second temperature is between about 55° C. and about 80° C.

* * * * *